(12) United States Patent
Hassan et al.

(10) Patent No.: US 8,044,220 B2
(45) Date of Patent: Oct. 25, 2011

(54) HIGH SHEAR PROCESS FOR THE PRODUCTION OF BUTADIENE SULFONE

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 553 days.

(21) Appl. No.: 12/137,448

(22) Filed: Jun. 11, 2008

(65) Prior Publication Data

US 2009/0005578 A1    Jan. 1, 2009

Related U.S. Application Data

(60) Provisional application No. 60/946,515, filed on Jun. 27, 2007.

(51) Int. Cl.
    *C07D 333/48*    (2006.01)
(52) U.S. Cl. .......................................... 549/80; 549/87
(58) Field of Classification Search .................... 549/80, 549/87
    See application file for complete search history.

(56) References Cited

U.S. PATENT DOCUMENTS

| 3,872,871 A | 3/1975 | Fiore et al. |
| 3,998,845 A | 12/1976 | Goldstein et al. |
| 5,108,662 A | 4/1992 | Litz et al. |
| 5,877,350 A | 3/1999 | Langer et al. |
| 6,135,430 A | 10/2000 | Bergman et al. |
| 6,368,366 B1 | 4/2002 | Langer et al. |
| 6,368,367 B1 | 4/2002 | Langer et al. |
| 6,383,237 B1 | 5/2002 | Langer et al. |
| 2003/0043690 A1 | 3/2003 | Holl |
| 2004/0052158 A1 | 3/2004 | Holl |
| 2005/0033069 A1 | 2/2005 | Holl et al. |

FOREIGN PATENT DOCUMENTS

| EP | 1925597 A1 | 5/2008 |
| WO | 98-31453 A1 | 7/1998 |
| WO | 99-07460 A1 | 2/1999 |

OTHER PUBLICATIONS

International Search Report, International Application No. PCT/US2008/066884, dated Dec. 24, 2008.

*Primary Examiner* — Taofiq A Solola
(74) *Attorney, Agent, or Firm* — Porter Hedges LLP; Timothy S. Westby

(57) ABSTRACT

Use of a high shear mechanical device incorporated into a process for the production of sulfolene as a reactor device is capable of decreasing mass transfer limitations, thereby enhancing the sulfolene production process. A system for the production of sulfolene from butadiene and sulfur dioxide, the system comprising a reactor and an external high shear mixer the outlet of which is fluidly connected to the inlet of the reactor; the high shear mixer capable of providing a dispersion of sulfur dioxide gas bubbles within a liquid, the bubbles having an average bubble diameter of less than about 100 μm.

14 Claims, 2 Drawing Sheets

HIGH SHEAR PROCESS FOR THE PRODUCTION OF BUTADIENE SULFONE

CROSS-REFERENCE TO RELATED APPLICATIONS

This application claims the benefit under 35 U.S.C. §119(e) of U.S. Provisional Patent Application No. 60/946,515 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of butadiene sulfone from reaction of butadiene and sulfur dioxide, and more particularly to apparatus and methods for producing butadiene sulfone via liquid phase (4+1) cycloaddition between butadiene and sulfur dioxide. More specifically, the disclosure relates to the reduction of mass transfer limitations in apparatus and methods for converting sulfolene to butadiene sulfone.

2. Background of the Invention

The present disclosure relates to the production of butadiene sulfone, also known as sulfolene. Sulfolene is a cyclic monosulfone that is used as a chemical intermediate for many industrially significant products such as pure butadiene. Additionally, sulfolene can be readily hydrogenated to sulfolane, which is a valuable selective solvent for many organic substances, as well as a thermally stable inert reaction medium.

Conventionally, the method for preparing sulfolene includes mixing a significant molar excess of liquid butadiene, with liquid sulfur dioxide under non-aqueous conditions. During this method the reactants are mixed at pressures between 100 and 500 pounds per square inch and at a temperature of about 100° C. In certain cases, a substituted diene may be used. However, the reaction times for this conversion are considered excessively long, and can be as high as two days. Furthermore, sulfur dioxide and butadiene in this conventional processes form insoluble polymeric butadiene sulfones; generally those conditions which increase the reaction rate for the sulfolene reaction also increase the rate for the undesirable polymer reaction. Research and development has primarily focused on the development of systems to prevent the formation of the polysulfones.

For example, a process of applying polymer inhibitors to prevent formation of the polysulfone has been disclosed in U.S. Pat. No. 2,443,270. Sodium hydroxide washing of the butadiene to eliminate peroxides, which favor the formation of polymer, has been disclosed, for example in U.S. Pat. No. 2,420,834. Other conventional techniques have strived to improve results by controlling the temperature of the reaction, for example, U.S. Pat. Nos. 2,402,891 and 2,395,050. Other procedures describe the preparation of sulfolene in alcohols or other organic substances, for example, U.S. Pat. No. 3,077,479 and German Pat. No. 506,839.

Accordingly, there is a need in the industry for improved processes for the production of butadiene whereby effective conversion is obtained. For example, systems for sulfur dioxide and butadiene conversion to butadiene sulfone are desired; with reduced costs, improved characteristics such as, yield, temperature, pressure, reaction time, and/or reduced capital and/or operating costs.

SUMMARY OF THE INVENTION

A high shear system and process for accelerating sulfolene production is disclosed. The high shear process makes possible a reduction in mass transfer limitations, thereby increasing the reaction rate and enabling a reduction in reactor temperature, a reduction in reactor pressure, a reduction in contact time, and/or an increase in product yield. In accordance with certain embodiments of the present invention, a process is provided that makes possible an increase in the rate of a liquid phase process for the production of sulfolene from butadiene by providing for more optimal time, temperature and pressure conditions than are currently used.

The process employs an external high shear mechanical reactor to provide enhanced time, temperature and pressure conditions resulting in accelerated chemical reactions between multiphase reactants.

In an embodiment, the process comprises the use of an external pressurized high shear mixer reactor to provide for production of sulfolene without the need for large volume reactors and substantial unconverted butadiene recovery.

These and other embodiments, features and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
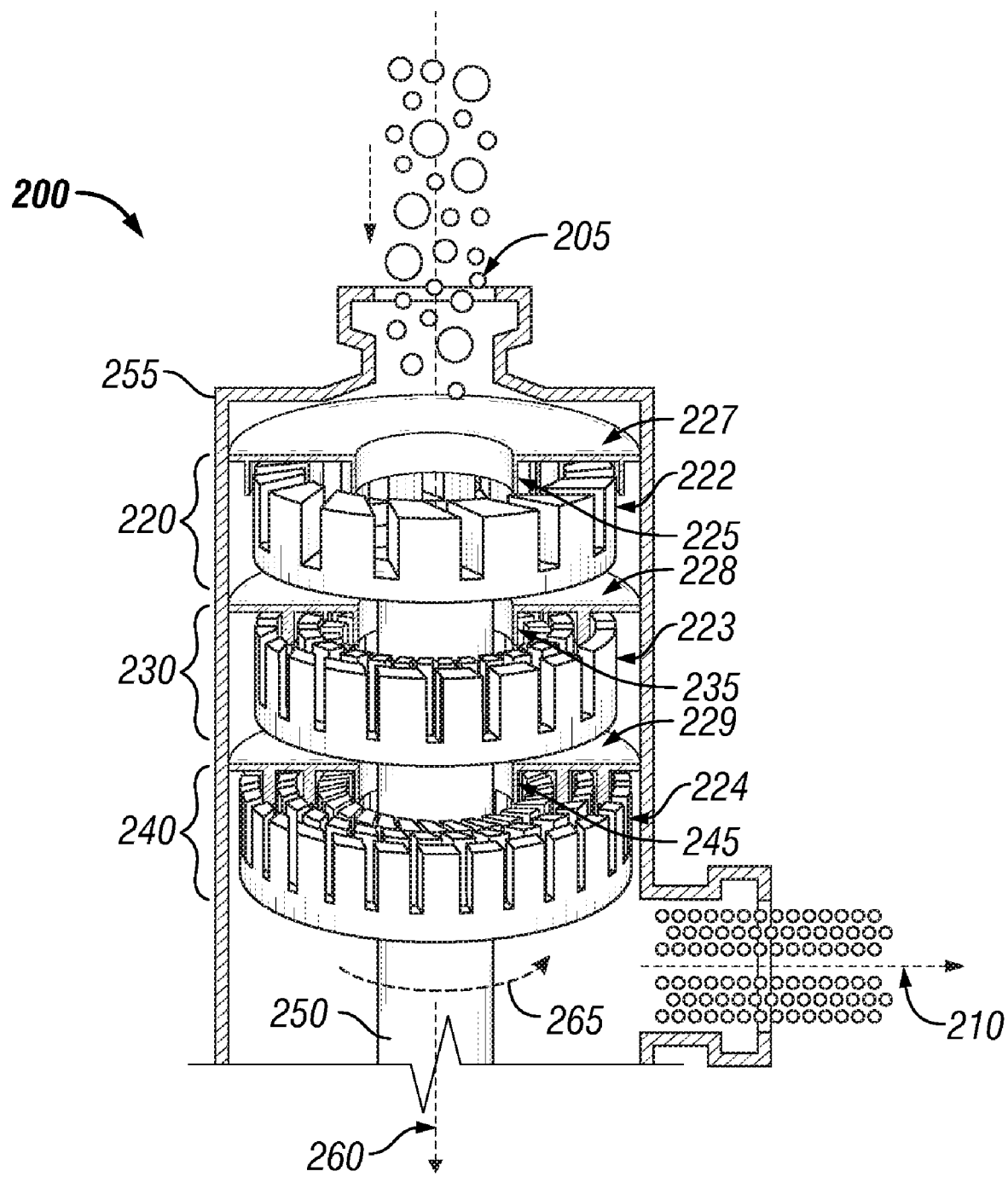
FIG. 1 is a cross-sectional diagram of a high shear device for production of sulfolene.

A high shear system and method for accelerating the liquid phase reaction of butadiene with sulfur dioxide employs a high shear mechanical device to provide rapid contact and mixing of chemical ingredients in a controlled environment in the reactor/mixer device. The high shear device reduces the mass transfer limitations on the reaction and thus increases the overall reaction rate for the conversion to butadiene sulfone.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants.

In conventional reactors, contact time for the reactants and/or catalyst is often controlled by mixing which provides contact with two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 µm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m³. In embodiments, the energy expenditure is in the range of from about 3000 W/m³ to about 7500 W/m³. The shear rate generated in a high shear device may be greater than 20,000 $s^{-1}$. In embodiments, the shear rate generated is in the range of from 20,000 $s^{-1}$ to 100,000 $s^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least 1034 MPa. In further embodiments, the pressure is dependent on the viscosity of the solution, rotor tip speed, and shear gap.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 μm; preferably the bubbles are sub-micron in diameter. In certain instances, the average bubble size is in the range from about 1.0 μm to about 0.1 μm. Alternatively, the average bubble size is less than about 400 nm (0.4 μm) and most preferably less than about 100 nm (0.1 μm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 μm in diameter may comprise a micro-foam.

Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described above. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300-700 l/h (depending on generator), a tip speed of from 9.4-41 m/s (about 1850 ft/min to about 8070 ft/min). Several alternative models are available having various inlet/outlet connections, horsepower, nominal tip speeds, output rpm, and nominal flow rate.

Description of High Shear Sulfolene Production Process and System

U.S. Pat. No. 3,998,845 describes a process wherein sulfolene is efficiently produced by reacting sulfur dioxide with an aqueous suspension or emulsion of butadiene in approximately equal molar amounts using a quantity of non-oxygenating water sufficient at least to dissolve all sulfolene formed by the reaction. Conversions in excess of 50% and generally higher than 80% are reported, with reaction times ranging from one to three hours. Of the reaction product obtained, 65 to 100% is sulfolene while the remainder is the sulfone polymer. Sulfolene is very soluble in hot water, while the polymeric sulfone is very insoluble in water. Sulfolene dissolves in the aqueous medium virtually as rapidly as formed. As a result, the sulfolen can be easily and virtually automatically separated by filtration of the hot aqueous reaction mixture, thereby avoiding any complicated purification procedures or operations. A further advantage of the aqueous process is that the excess sulfur dioxide is readily removed as a gas at the end of the reaction, and none is present in the finished product. This feature is important to the hydrogenation of the sulfolane to sulfolene, as it eliminates the necessity for costly purification process.

Figure 2:
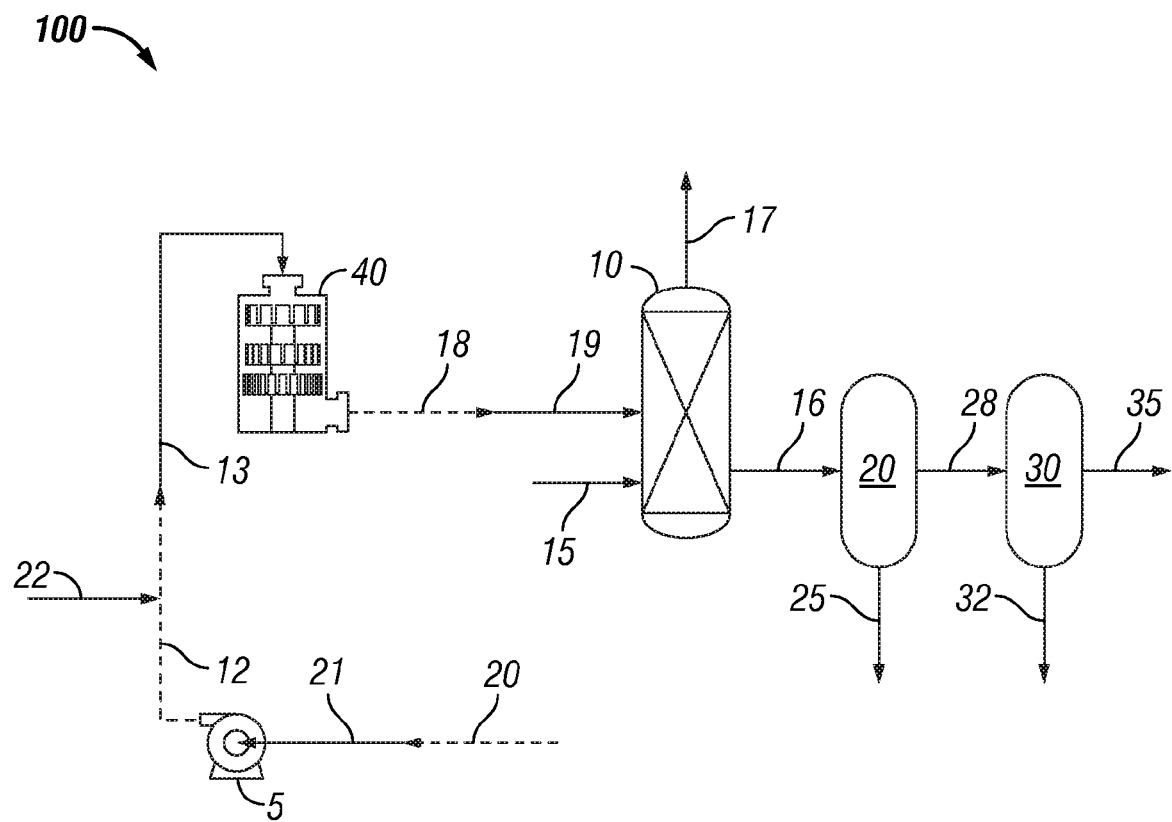
FIG. 2 is a process flow diagram according to an embodiment of the present disclosure for a mediator-assisted high shear process for production of sulfolene

The high shear sulfolene production process and system of the present disclosure will now be described in relation to FIG. 2 which is a representative process flow diagram of a high shear system (HSS) 100 for the production of sulfolene from butadiene and sulfur dioxide. FIG. 2 illustrates the basic components of a representative high shear sulfolene system (HSS) 100. These components comprise pump 5, high shear device (HSD) 40, and reactor 10. The HSS 100 produces an emulsion comprising butadiene, water and gaseous sulfur dioxide. In certain embodiments water comprises de-aerated, or non-oxygenating water.

In embodiments, water is rendered nonoxygenating by use of an antioxidant as described in U.S. Pat. No. 3,998,845 which is incorporated herein for all purposes in its entirety. Use of water as the continuous reaction phase is not necessary, but may increase sulfolene to the 80 to 100% level with a corresponding drop in the amount of polysulfone. In embodiments, the antioxidants comprises alkyl mercaptan, an inorganic salt of inorganic lower valence sulfur acid, an inorganic salt of inorganic lower valence phosphorous acid, or a mixture thereof. Examples of suitable antioxidants include sodium dithionite, sodium hypophosphite, sodium sulfide, sodium sulfite, n-octyl mercaptans, n-butyl mercaptan, and t-butyl catechol. As much as the sulfolene reaction is conducted under acidic conditions, the selected antioxidant must be able to function in an acid medium. Sodium dithionite and sodium sulfide, are acid unstable compounds are disclosed in U.S. Pat. No. 3,998,845 to be readily applicable for use. In embodiments, the reaction stream comprises 0.1 to 15 parts antioxidant per 1000 parts of water. Alternatively, the antioxidant level is 2.5 to 7 parts per 1000 parts of water used.

Pump 5 is used to provide a controlled flow throughout high shear device 40 and high shear sulfolene system 100. Pump inlet stream 21 comprises de-aerated water. Pump inlet stream 21 may further comprise butadiene. Pump 5 increases the pressure of the pump inlet stream 21 to greater than about 203 kPa (about 2 atm); alternatively, the inlet stream 21 is pressurized to greater than about 304 kPa (about 3 atm). Additionally, pump 5 may build pressure throughout HSS 100. In this way, HSS 100 combines high shear with pressure to enhance reactant intimate mixing. Preferably, all contact parts of pump 5 are stainless steel, for example, 316 stainless steel. Pump 5 may be any suitable pump, for example, a Dayton Pressure Booster Pump Model 2P372E, Dayton Electric Co (Niles, Ill.).

The pressurized aqueous solution exits pump 5 via pump exit stream 12. Pump exit stream 12 may further comprise a pressurized aqueous solution of butadiene. Pump exit stream 12 is mixed with dispersible gas stream 22, comprising sulfur dioxide. Dispersible gas stream 22 is injected into pump exit stream 12. Pump exit stream 12 is in fluid communication with high shear device inlet stream 13. HSD inlet stream 13 comprises dispersible reactant stream 22 and pump exit stream 12. HSD inlet stream 13 may be coupled directly to pump 5, such that HSD inlet stream 13 and pump exit stream 12 comprise the same stream. Dispersible reactant stream 22 and pump exit stream 12 are introduced separately, or simultaneously, to the HSD inlet stream 13. In a preferred embodiment, sulfur dioxide gas may continuously be injected into HSD inlet stream 13. HSD inlet stream 13 is in fluid communication with high shear device (HSD) 40.

High shear device 40 serves to intimately mix pump exit stream 12 with dispersible reactant stream 22. As discussed in detail above, HSD 40 is a mechanical device that utilizes, for example, a stator rotor mixing head with a fixed gap between the stator and rotor. High shear device 40 mixing results in an emulsion of sulfur dioxide gas in the aqueous butadiene solution comprising micron or sub micron diameter gas bubbles. The emulsion comprises microbubbles. Preferably, the emulsion comprises bubbles in the submicron size, or a microfoam. In HSD 40, dispersible gas stream 22 and pump exit stream 12 are highly dispersed to form an emulsion comprising an average gas particle, or bubble, diameter less than about 1.5 µm; preferably the bubble diameters are about submicron. In certain instances, the average bubble diameter is in the range from about 1.0 µm to about 0.1 µm. Alternatively, the average bubble diameter is less than about 400 nm (0.4 µm) and most preferably less than about 100 nm (0.1 µm). In certain instances, the emulsion comprises microfoam. Further, the high shear device produces sulfur dioxide bubbles capable of remaining dispersed in the emulsion at atmospheric pressure for about 15 minutes. In certain embodiments there may be a plurality of high shear device 40 used in series or in parallel.

In certain instances, the high shear device 40 is incorporated into an established process, thereby enabling an increase in production (i.e., greater throughput). Without wishing to be limited to a particular theory, it is believed that the level or degree of high shear mixing is sufficient to increase rates of mass transfer and also produces localized non-ideal conditions that enable the reactions to occur that would not otherwise be expected to occur based on Gibbs free energy predictions. The localized non ideal conditions are believed to occur within the high shear device resulting in increased temperatures and pressures with the most significant increase believed to be in localized pressures. The increase in pressures and temperatures within the high shear device are instantaneous and localized and quickly revert back to average system conditions once exiting the high shear device.

The emulsion exits HSD 40 by HSD outlet 18. HSD outlet 18 is introduced into reactor 10 as reactor inlet stream 19. Alternatively, HSD outlet 18 may undergo further processing prior introduction to reactor inlet stream 19. Reactor inlet stream 19 is in fluid communication with reactor 10 wherein sulfolene production occurs. Water is the continuous phase for the reaction system as well as the solvent for the sulfolene product. In embodiments, reactor 10 yields a saturated aqueous solution of sulfolene product. This indicates the initial presence of between about 80 parts butadiene to about 180 parts butadiene per 100 parts of water. In specific embodiments, reaction occurs with a fraction of that level in order to maintain complete control over the reactions.

Reactor 10 is any type of reactor in which the reactions described herein can be executed. Reactor 10 is a continuous stirred tank reactor. Reactor 10 may be configured for maintaining high than about atmospheric pressure and higher than about ambient temperature. In certain instances reactor pressure may be in the range of from about 100 kPa to about 3800 kPa. The reaction temperature may be in the range of from about 60° C. to about 150° C.

In certain instances, HSS 100 comprises second inlet stream 15, comprising an aqueous solution. Second inlet stream 15 comprises butadiene or other reactants as known to one skilled in the art. Second inlet stream 15 may be injected or fed directly into reactor 10. In further instances, second inlet stream 15 may be injected into HSS 100 in alternative locations.

HSS 100 may comprise additional components to maintain reactor 10 at a preferred reaction temperature. In certain embodiments, HSS 100 comprises cooling coils in the reactor 10 to maintain reaction temperature, as known to those of skill in the art. Alternatively, a thermal jacket or exterior heat exchanger may be used. To maintain favorable reaction temperatures, HSS 100 may comprise at least one heat exchanger located elsewhere in the system. Suitable locations for heat exchangers include, but are not limited to, between the reactor 10 and the pump 5; between the pump 5 and the HSD 40; between HSD 40 and the reactor 10. For example, suitable heat exchangers include plate, coil, and shell and tube designs, without limitation.

Reactor 10 further comprises an emulsifying agent which functions under acidic conditions. Reactor 10 comprises about 0.05% to 1.0%, based on the weight of water, of an emulsifying agent which may be an anionic, cationic, nonionic, or amphoteric emulsifier. Suitable emulsifiers include sodium lauryl sulfate, sulfonated fatty acid derivatives, sulfonates, sulfates, aliphatic phosphate esters, alkanolamides, heterocyclic acids, substituted sarcosinates, salts of sulfosuccinate derivatives of fatty acids, salts of dodecyl sulfate, salts of alkyl aryl sulfonates, salts of mono- or di-alkyl phosphoric acids, amphoteric salts of fatty acid 2-imidazolinyl compounds, salts of fatty alcoyl sarcosine, fatty acid alkanolamides and polyethoxylated alkyl phenols.

Although butadiene is the preferred conjugated diene monomer with regard to the process of this invention, other diene monomers may effectively be utilized therein. It is thus appropriate to characterize the applicable diene monomers in terms of the following formula: $R_1R_2C\!=\!CR_3CR_4\!=\!CR_5R_6$ wherein $R_1$, $R_2$, $R_3$, $R_4$, $R_5$ and $R_6$ are independently selected from the group consisting of hydrogen atoms and alkyl, alkenyl, aryl, alkoxy, alkaryl, aralkyl, cycloalkyl, cycloalkenyl and halogen radicals. Suitable conjugated diene monomers include butadiene-1,3; 2-methyl butadiene-1,3 (isoprene); pentadiene-1,3 (piperylene); 2,3-dimethyl butadiene1,3; 2,3-diethyl butadiene-1,3; 2,3-di-tertiary-butyl butadiene1,3; 2-tertiary-butyl butadiene-1,3; 1,2,3,4-tetramethyl butadiene-1,3; 1,4-dimethyl-2,3-diethyl butadiene-1,3; 2-methyl pentadiene-1,3; 4-methyl pentadiene-1,3; 2-methyl hexadiene-1,3; 4-ethyl hexadiene-1,3; cyclopentyl butadienes; cyclohexyl butadienes; cyclopentyl hexadienes; 2-phenyl butadiene-1,3; 2-chlorbutadiene-1,3; 2-methyl-3-chlorbutadiene-1,3; 3-methoxybutadiene-1,3; and the like. Needless to say, the use of any of these materials will result in the preparation of the correspondingly substituted sulfolene product, and the term "sulfolene compound" as used herein and in the claims includes the compound "sulfolene" and such substituted sulfolene products. For purposes of this disclosure, statements attributed to butadiene are equally applicable to any of these diene monomers. Diolefinic conjugated hydrocarbons, like butadiene, are relatively insoluble in water.

Reactor 10 reaction may comprise between about 50 parts by weight and about 1700 parts by weight butadiene, more preferably between about 800 parts by weight and about 1200 parts by weight butadiene, and most preferably about 1000 parts by weight butadiene. Further, reaction comprises between about 60 parts by weight sulfur dioxide and about 1900 parts by weight sulfur dioxide, between about 0.5 parts by weight emulsifier and about 10 parts by weight emulsifier, and between about 0.1 parts by weight antioxidant and about 15 parts by weight antioxidant.

The sulfur dioxide is dispersed in water it produces a pH of about 2.0. Thus, the reaction in aqueous systems between sulfur dioxide and butadiene occurs under acidic conditions because of the sulfur dioxide dissolved therein. In embodiments, excess sulfur dioxide gas is removed from reactor 10 by gas exit 17. This is advantageous when sulfolene is to be further hydrogenated to form sulfolane, as it eliminates costly purification steps Gas exit 17 is configured for removal of gas containing unreacted sulfur dioxide, any other reaction gases and/or pressure. Gas exit 17 may vent the head space of the reactor 10. Gas exit 17 may comprise a compressor, or other device as known to one skilled in the art, to compress gasses removed from the reactor 10. Additionally, gas exit 17 recirculates gases to the high shear device 40. Recycling the unreacted gases from reactor 10 may serve to further accelerate the reactions.

Reaction products exit reactor 10 through reactor product stream 16. Sulfolene produced in the reactor 10, dissolves in the aqueous medium as it is formed, and remains dissolved in reactor product stream 16. However the polymeric sulfone is insoluble in water, and requires filtering to remove. Reactor product stream 16 may comprise a heater configured to maintain a temperature of at least about 70° C. Reaction product stream 16 comprising sulfolene may be heated to at least about 85° C. prior to introduction to filter 20. Reaction product steam 16, once heated, is preferred for filtering the polymeric sulfone from the sulfolene. Filter 20 to removes polymer formed during the reaction from the product stream 16 by polymer stream 25. Hydrogen sulfide is removed by treating the product stream 16 with sodium bicarbonate to form sodium sulfite.

Sulfolene may be recovered by crystallizing it out of solution by cooling the reaction mixture to at or below room temperature and separating the sulfolene by separator 30. Separator 30 may comprise, for example, a centrifuge or filter. Separator 30 divides filtration product stream 28 yielding sulfolene product stream 35 and solvent stream 32. Sulfolene product stream 35 may comprise a solid product.

If water is recovered from solvent stream 32, the recovered water may be recycled and reused. The sulfolene product stream 35 may be further purified by recrystallizing it from water and/or alcohol a second time. The final product, after separation of the sulfolene solids by means such as filtering, may be vacuum dried and stored for future use, or may be hydrogenated to the saturated compound, sulfolane, as known to those of skill in the art.

In embodiments, use of the disclosed process comprising reactant mixing via external high shear mixer 40 allows greater conversion of butadiene to sulfolene and/or an increase in throughput. In embodiments, the method comprises incorporating external high shear mixer 40 into an established process thereby enabling the increase in production (greater throughput) from a process operated without high shear mixer 40. The superior dissolution provided by the high shear mixing may allow a decrease in operating pressure while maintaining or even increasing reaction rate and/or may reduce production of undesirable polysulfone.

In embodiments, the method and system of this disclosure enable design of a smaller and/or less capital intensive process than previously possible without the incorporation of external high shear mixer 40. In embodiments, the disclosed method reduces operating costs/increases production from an existing process. Alternatively, the disclosed method may reduce capital costs for the design of new processes. Potential benefits of this modified system and method for the production of sulfolene include, but are not limited to, faster cycle times, increased throughput, reduced operating costs and/or reduced capital expense due to the possibility of designing smaller reactors and/or operating the sulfolene production at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

What is claimed is:

1. A method for producing sulfolene, the method comprising
    contacting butadiene with sulfur dioxide wherein sulfur dioxide gas is provided as gas bubbles having a mean diameter less than about 5 μm, at a pressure less than about 500 psig and a temperature less than about 150° C.

2. The method of claim 1 wherein the gas bubbles have a mean diameter of less than about 100 nm.

3. The method of claim 1 further comprising providing sulfur dioxide gas as a dispersion of gas bubbles in deaerated water.

4. The method of claim 1 further comprising providing sulfur dioxide gas as a dispersion of gas bubbles butadiene.

5. The method of claim 3 further comprising introducing sulfur dioxide gas and deaerated water into an external high shear mixer to produce a dispersion of gas.

6. The method of claim 5 wherein the high shear mixer comprises a high shear mill having a nominal tip speed of greater than 1000 ft/min.

7. The method of claim 6 wherein the high shear mixer comprises a high shear mill having a nominal tip speed of greater than 4000 ft/min.

8. The method of claim 1 wherein the reaction medium further comprises an antioxidant.

9. A system for the production of sulfolene from butadiene, the system comprising;
    an external high shear mixer which produces a dispersion of sulfur dioxide in liquid medium, the dispersion having an average bubble diameter of less than about 100 nm; and
    a reactor wherein sulfolene is produced from the reaction of sulfur dioxide with butadiene; the reactor fluidly connected to the outlet of the external high shear mixer.

10. The system of claim 9 wherein the high shear mixer comprises a high shear mill having a nominal tip speed of greater than 1000 ft/min.

11. The system of claim 10 wherein the high shear mixer has a nominal tip speed of greater than 4000 ft/min.

12. In a system for production of sulfolene from hydrogen sulfide and butadiene, including a reactor operating at conditions suitable for the cycloaddition reaction of butadiene with sulfur dioxide to yield sulfolene, the improvement comprising: inserting a high shear mixer upstream of said reactor, said high shear mixer comprising a liquid inlet and a sulfur dioxide gas inlet, and producing a high shear feed stream to said reactor unit wherein said feed stream comprises gas bubbles of no more than about 100 nm in diameter.

13. The system of claim 12 wherein the high shear mixer comprises a high shear mill having a nominal tip speed of greater than about 1000 ft/min.

14. The system of claim 13 wherein the high shear mixer has a nominal tip speed of greater than about 4000 ft/min.

* * * * *